(12) United States Patent
Li (10) Patent No.: US 10,251,793 B1
(45) Date of Patent: Apr. 9, 2019

(54) INTELLIGENT INCONTINENCE MONITOR GENERATING AND UTILIZING INCONTINENCE PROFILES

(71) Applicant: Edward Li, San Diego, CA (US)

(72) Inventor: Edward Li, San Diego, CA (US)

( * ) Notice: Subject to any disclaimer, the term of this patent is extended or adjusted under 35 U.S.C. 154(b) by 0 days.

(21) Appl. No.: 15/939,172

(22) Filed: Mar. 28, 2018

(51) Int. Cl.
*A61F 13/42* (2006.01)
*A61B 5/00* (2006.01)
*A61F 5/48* (2006.01)
*A61B 5/20* (2006.01)
*H01Q 1/22* (2006.01)

(52) U.S. Cl.
CPC ............. *A61F 13/42* (2013.01); *A61B 5/002* (2013.01); *A61B 5/202* (2013.01); *A61F 5/485* (2013.01); *A61F 2013/421* (2013.01); *A61F 2013/424* (2013.01); *A61F 2013/427* (2013.01); *H01Q 1/2208* (2013.01)

(58) Field of Classification Search
CPC .... A61F 13/42; A61F 5/485; A61F 2013/421; A61F 2013/424; A61F 2013/427; A61B 5/002; A61B 5/202
USPC ............... 340/573.5, 604, 572.1, 539.1, 505
See application file for complete search history.

(56) References Cited

U.S. PATENT DOCUMENTS

| | | | | |
|---|---|---|---|---|
| 6,774,800 B2 * | 8/2004 | Friedman | ............ | A61B 5/0002 340/572.5 |
| 7,250,547 B1 * | 7/2007 | Hofmeister | ............ | A61F 13/42 340/573.5 |
| 8,237,572 B2 * | 8/2012 | Clement | ............ | A61F 13/42 340/10.1 |
| 8,978,452 B2 * | 3/2015 | Johnson | ............ | G01N 27/223 73/74 |
| 9,160,054 B2 * | 10/2015 | Yu | ............ | H01Q 1/2225 |
| 2002/0145526 A1 * | 10/2002 | Friedman | ............ | A61B 5/0002 340/573.5 |
| 2011/0263952 A1 * | 10/2011 | Bergman | ............ | A61F 13/42 600/309 |
| 2012/0268278 A1 * | 10/2012 | Lewis | ............ | A61F 13/42 340/573.5 |
| 2017/0065464 A1 * | 3/2017 | Heil | ............ | A61F 13/42 |
| 2017/0098044 A1 * | 4/2017 | Lai | ............ | G06K 19/0716 |
| 2017/0162931 A1 * | 6/2017 | Young | ............ | H01Q 1/2291 |
| 2018/0021184 A1 * | 1/2018 | Monson | ............ | G16H 40/20 340/573.5 |
| 2018/0221216 A1 * | 8/2018 | Benz | ............ | A61F 13/42 |

* cited by examiner

*Primary Examiner* — Adnan Aziz
(74) *Attorney, Agent, or Firm* — Continuum Law; Robert P. Cogan (57) ABSTRACT

A system comprises a series of passive RFID tag sensors each embedded on top of its own matching antenna inside a flexible substrate. The sensors are driven by a controller-transceiver. The controller-transceiver sends RF signals through an antenna to each RFID tag sensor and receives data transmitted back from the same sensors. Sensors are embedded in a flexible substrate positioned under an unaltered incontinence absorbent pad and juxtaposed to derive further information. Multiple sensors provide sensing of physical-environmental data in addition to moisture. The controller makes intelligent and positive incontinence determinations by relating data to profiles indicative of correlation to incontinence conditions.

25 Claims, 6 Drawing Sheets

INTELLIGENT INCONTINENCE MONITOR GENERATING AND UTILIZING INCONTINENCE PROFILES

FIELD

The present subject matter relates to an incontinence monitoring system utilizing a plurality of embedded radio frequency identification (RFID) tag sensors in a flexible mat to detect incontinence on a discrete absorbent pad to generate and use incontinence profiles.

BACKGROUND

Incontinence is a condition suffered by many patients in facilities such as nursing homes, acute care facilities, and intensive care units (ICUs). The traditional solution has been to clothe patients in diapers. Commonly, patients are not changed frequently enough. Continued contact of the skin with body waste leads to complications such as Incontinence-Associated Dermatitis (IAD), known familiarly as "diaper rash." IAD can further develop into pressure ulcer (PU) and other secondary skin infections. According to *Changing Our Methods of Adult Incontinence Management to Decrease Skin Breakdown and Improve Patient Satisfaction,* 42nd Wound, Ostomy & Continence Nurses Society Conference, Jun. 12-16, 2010, 78% of acute-care hospitalized adult patients wearing diapers suffered from these conditions. Among incontinence patients in residential care facilities, half were urinary incontinent only, according a CDC Study, *Prevalence of Incontinence Among Older Americans, CDC Vital And Health Statistics, June,* 2014. The same Study also found that individuals who are incontinent may carry an emotional burden of shame and embarrassment in addition to the physical discomfort and disruption of their lives that occur with episodes of incontinence.

Major metropolitan hospitals have eliminated diapers in favor of underpads due to IAD. Underpads, disposable absorbent towels made with layered absorbent material, are preferable to diapers because they minimize the contact area between skin and waste that causes IAD. Incontinence hospital patients are now placed on underpads while wearing open-back gowns. Changing an underpad is simple in comparison to changing a diaper.

In as much as underpads are less likely to cause diaper rash than diapers because there is more room for air circulation, IAD is still a danger as long as there is prolonged exposure of the skin to urinary discharge. The timely changing of diapers and underpads is the cure for IAD. However, prior art systems have shortcomings in timely notification of staff.

For alert and demanding suffering patients, assistance call bells for each institutional bed would be activated. Depending on the staff ratio and the existing level of care at the facility, calls may or may not be responded to as timely as desired. Also, assistance calls are not specific on the nature and severity of the call, and nurses are usually the first responders. Incontinence is most economically handled by nurses' aides. A specific and automatic incontinence alarm can be more effective in-patient care, be it IAD or the psychological scourge of loss of dignity when incontinence is not handled expeditiously. Lower functioning patients may not even be aware of their incontinence to call for help.

Many approaches have been taken in the prior art to provide a sensor embedded in a multilayer absorbent article in order to indicate an incontinence event. In this manner, a patient can be attended to when there is a need rather than on a predetermined time schedule.

Prior approaches have been embodied primarily in diapers. A number of these approaches utilize radio frequency (RF) resonance, and recently, radio frequency identification (RFID) incorporating advances in this technology. RFID is familiar to consumers as the technology that permits vehicle owners of RFID identification devices to bypass toll booths and enter secured garages without stopping. RFID offers added identification capability to RF resonance detection. User and usage data can now be recorded and retrieved wirelessly. Most RFID systems continuously emit high frequency RF in the same manner as cell phones being left on to respond to incoming calls. Recent government reports correlate continuous cell phone usage with brain disease. An RFID system that does not require continuous radio frequency emissions eliminates or reduces concern as to this correlation.

An RFID tag primarily comprises an antenna and assorted electronic components to enable 2-way communication between tag and transceiver. A passive tag is not powered; but when its antenna resonates with a signal generated by its mating transceiver, the energy received powers on the tag integrated circuit to activate the tag. Passive RFID tags can be queried via a frequency with which the antenna is resonant. In response to excitation with a resonant frequency, the resonating antenna provides energy which can be stored in a capacitor which functions similar to a microminiature rechargeable battery. Passive RFID tags are more convenient to use than active, powered RFID tags because they do not depend on battery or external power to work and are suitable for reporting ID and other information.

Antenna impedance changes in the proximity of certain materials. An example is when the RFID tag is close to objects with high capacitance. A human body with its very high water content can detune both the RFID tag and the antenna. Most RFID tags of varying operating frequencies are affected by the proximity of the human body in the same manner. Thus, RFID sensor tags can use impedance change at its antenna to sense objects which induce changes in the antenna characteristics. Recent technical advances allow RFID tags to serve as sensors for certain material attributes rather than merely providing identification. Each type of RFID sensor tag is calibrated to the characteristics of a specific physical attribute such as moisture or temperature or gas or pressure, to name a few of the currently available types.

There is an RFID moisture sensor tag on the market that demonstrates on its web site (https://www.youtube.com/watch?v=meB9imQN0HU&feature=youtu.be) that the product can be used to detect wet diaper. The demonstration consists of pouring water on a dry diaper with a moisture sensor tag attached and a hand-held RFID reader to detect moisture reading. This video does not address the situation of a diaper on a real body. Because the human body holds enough moisture to trigger a "wet" reading when the dry diaper is wrapped around the patient, there will be false positive reading errors since body capacitance has not been factored out. This prior art system also requires a caregiver to tape a moisture sensor RFID tag on a diaper and periodically read the sensor output on bed inspection rounds unless the patient calls out for service before the manual scanning. Sanitation concerns will also mean that the sensor will be disposed along with the wet diaper.

United States Published Patent Application No. 20020145525 discloses a diaper comprising a plurality of RFID tags. Each of the RFID tags is coated with a dry electrolyte which enhances response to moisture. Each tag is also assigned a unique frequency. The sequence and relative response of tags to enquiring signals indicate position and moisture status. Because of the design complexity, implementation can be costly.

United States Published Patent Application No. 20140358099 discloses a system embedded in a diaper including first and second RFID tags respectively placed on an upper end and a lower end of a diaper with a moisture strip connected to both tags. This construction requires special fabrication to connect the RFID tags and the sensor. Standard, off-the-shelf components cannot be used.

U.S. Pat. No. 8,502,684 discloses a diaper with dissolvable conductive moisture sensor traces connected to an RFID tag antenna. Initial moisture contact will not completely dissolve the traces, and an antenna impedance change will indicate initial moisture. A positive incontinence condition is indicated by complete dissolution of the traces, with the RFID antenna not functioning. Lack of response is indistinguishable from a complete failure. Special materials must be used for the conductive traces to avoid breaks during handling and in in situ wearing conditions U.S. Pat. No. 6,876,303 discloses a system for monitoring hospital personnel, a plurality of patient locations for patients and associated devices having a plurality of patient controls. Transmitters carried by each of a plurality of hospital personnel each periodically transmit a signal unique to that transmitter. The signal could indicate a patient or sensor triggered event alarm. A computer coupled to the associated devices is configured to respond to disable at least one of the patient controls while hospital personnel attend to the patient. This arrangement monitors hospital personnel and not patients nor their need status.

U.S. Pat. No. 8,237,572 and other patents, including U.S. Pat. No. 8,248,249 disclose an RFID tag and a system and method involving a plurality of RFID tags. Each RFID tag is attached to an object or to a structure or a person on which the presence of a predefined fluid is monitored. In a first state, absence of the monitored fluid, the tag is acting as a passive RFID tag and the information it holds can be read with a proximity RFID reader. This operation is performed when the RFID tag is attached to the object to be monitored. At this stage a table associating tag ID, object name and location may be built, and may be recorded so that information it contains is accessible by a control center. In a second state, whenever the monitored fluid appears on the tagged object, a fluid activated battery generates the electrical power which is used to power the RFID tag. The RFID tag then acts as an active RFID tag and starts to emit messages which can be received by a distant RFID reader. Alert messages include at least the tag ID but may comprise additional information like a name or a location. This system relies on activation of a battery by the salts in incontinence waste fluid which requires specially built components.

U.S. Pat. No. 8,196,809 discloses a system including a reader and an absorbent article containing machine-readable information identifying the user associated with the absorbent article and the user's location. A computer uploads data from the reader and stores the identifying information. On retrieval of information from the computer memory, information concerning the absorbent article is automatically associated with the identity and location of a user of the absorbent article. This disclosure is only concerned with inventory of the absorbent article; no live usage condition sensing is involved. This arrangement does not provide the benefit of monitoring the in situ status of the incontinence article as well as identification of its user and location.

United States Published Patent Application No. 20170224554 discloses a sensor system for detecting a property of or within an absorbent article which may comprise the absorbent article and a sensor. The sensor is a multi-use sensor for detecting the property. The sensor is configured for temporary attachment to and removal from the absorbent article, and still presents the difficulties of requiring custom assembly by medical staff.

SUMMARY

Briefly stated, in accordance with the present subject matter, there are provided a sensor module system for monitoring incontinence measuring parameters in addition to moisture. Incontinence profiles are generated and utilized to facilitate expeditious attention to patient needs in a home or institutional setting. An RFID tag sensor incontinence monitoring system is provided in which sensors are not inserted in or connected to sensors in an absorbent article, e.g., a diaper or an underpad. Incontinence management is accomplished with generic absorbent articles while intelligent monitoring is performed entirely in the background.

The present subject matter utilizes selected subject matter disclosed in commonly invented U.S. Pat. No. 9,649,230. The disclosure of U.S. Pat. No. 9,649,230 is incorporated herein in its entirety.

The sensor modules are embedded in a flexible substrate to form a sensor pad (elsewhere also referred to as sensor mat) to be placed below the patient and the bed sheet. The present prevailing nursing practice for urinary incontinence is an absorbent underpad placed on top of the bed sheet in registration with a patient's discharge orifice. The absorbent article layer holding the incontinence discharge triggers the alarm condition that calls attention to the incontinence event having occurred to require attention. In the present description an absorbent article may comprise an underpad or diaper. Absorbent articles, underpads or diapers, will be generic as available from incontinence supply manufacturers. "Generic" refers to a commercial off-the-shelf product. Furthermore, no sensor or accessory needs to be attached to the absorbent articles in any way for this monitor system to function.

Sensor modules are placed on a substrate of a soft, pliable material such as a suitable silicone polymer approved for use in hospitals. Each sensor module is composed of a RFID sensor tag on top of the substrate and an antenna below the substrate. This module design of 1 sensor tag with 1 external antenna will minimize the undesirable effects of individual tag antenna orientation, operating time, distance and other useful parameters common when a single external antenna is hub to multiple sensor tags, as in the case of using a single RFID reader-transceiver to obtain data from multiple RFID tag sensors. This sensor embedded substrate mat is placed beneath the incontinent patient fitted with any generic absorbent diaper or underpad. The passive RFID moisture tag sensor comprises an antenna on the tag calibrated to read antenna output and report the data to the controller-transceiver. A rewritable memory is included in each sensor tag integrated circuit (RFIC) to record ID and other patient medical information. The identifying information is programmed in the RFID tag when it is in the range of an RFID writer. This RFID writer can be the same RFID reader-writer that some hospitals use to encode patient RFID wristbands; or, alternatively, the present intelligent incontinence monitor system RFID reader-transceiver can be connected via WIFI or Bluetooth to an input device such as a cell phone or a keypad. Depending on hospital tracking requirements, the IDs in each sensor module on the pad may not need to be changed for each bed occupant. The sensor pad, once programmed for the hospital room, provides room ID which can be linked to the patient occupying the room in the hospital information system. The controller-transceiver provides RF excitation energy to operate each RFID sensor module in the sensor pad via a cable connection to each antenna. The custom controller-transceiver consistently interrogates each RFID sensor tag to detect incontinence signal profiles. When incontinence happens, data from each sensor module will alert the controller-transceiver separately. Each sensor module reports a different set of data depending on the embedded sensor type. Currently available RFID tag sensor types include moisture, temperature, gas, pH, and pressure. The controller, a customized microprocessor, will screen the various sensor data acquired in the RFID reader-transceiver using digital signal processing (DSP) algorithms matched to each physical-environmental attribute, e.g. moisture and its accompanying absorbance attribute, and others e.g., diffusion rate, temperature, pressure, etc., common to incontinence discharge in the absorbent article context. Hospital chosen brands and their respective absorbencies affect moisture reading and are taken into consideration in system installation. Each set of acquired data comprises a profile. Each profile of sensor data is then compared to a reference incontinence trigger profile stored in the controller memory. When there is a match, an alarm is generated for that particular physical-environmental attribute. The deployment of multiple sensor modules enables a different physical-environmental attribute to form a different data profile upon incontinence discharge. Multiple sensors allow redundancies to refine a logical positive determination and will minimize errors which can lead to false positives. False alarms may cause caretakers to be desensitized to alarms. Multiple sensors provide checks-and-balances to deter false positive incontinence calls which could happen with a single sensor. This system will also distinguish between leaks, which do not require absorbent change, and full rate incontinence flow based on reference saturation profiles. Finally, the controller will send the multiple sensor screened alarm response to caregivers via the hospital information system along with patient information encoded in the sensor tags. Such incontinence data can provide tracking on patient as well as patient care by providing time stamps on alarm and remediation. Patient medical record can also receive entries on incontinence frequencies, time, and material accounting as well as nursing response metrics.

DETAILED DESCRIPTION

The present subject matter may be used in the context of diapers or underpads. However, diapers are now banned in most large hospitals and institutions because diaper use in adult patients is linked to diseases in the covered skin areas. In its stead, underpads are placed under the body to catch incontinence discharge. To further minimize skin-waste contact, deployment of this system will notify caregivers when incontinence occurs to require replacement. In a preferred embodiment of an intelligent incontinence monitor system 10 (FIG. 4), a thin, flexible substrate is incorporated with multiple sensor modules. This thin substrate, presently referred to as a sensor pad 12, is a flexible, waterproof, and cleanable rectangle the size of a conventional underpad 100 (FIG. 5), covering the width of a hospital bed mattress 30. A nominal width is thirty inches or longer to match the dimension of the hospital's chosen underpad 100 type and size. This sensor pad 12 is placed to align with the patient discharge orifice immediately under a bed sheet 20 (FIG. 4) and on top of the mattress 30. The absorbent underpad 100 will be placed on top of the bed sheet 20 (FIG. 5) and in registration with the sensor pad 12. This sensor pad 12 can also accommodate a typical hospital diaper 49 (FIG. 6). Sensor modules 11, in the form of sets of RFID sensor tag 11A, insulator 11B and antenna 1C, are manufactured into the sensor pad 12. Sensor module 11 locations will vary depending on whether underpads 100 or diapers 49 are used. Ideally, there will be at least two or more sensor modules 11. The center sensor module 11-1, is in registration with the typical center location of the body, ideally matching the incontinence origination point. The second sensor module 11-2 would be located some distance farther downstream of the incontinence flow to catch and determine flow rate and volume. The center sensor module 11-1 can also act as a patient bed vacancy alarm since the sensor can sense a body accurately by its moisture content. First time pad installation may typically program the sensor tags 11A with the hospital room ID. To maximize this invention's full capability, each RFID sensor can be programmed with patient information for automated inventory, cost, billing, location tracking, and other data driven medical or business functionalities. Deployment of this system will enable the host hospital to fulfill Medicare and Affordable Care Act's twin mandates of disease prevention and cost-effective patient care.

Figure 1:
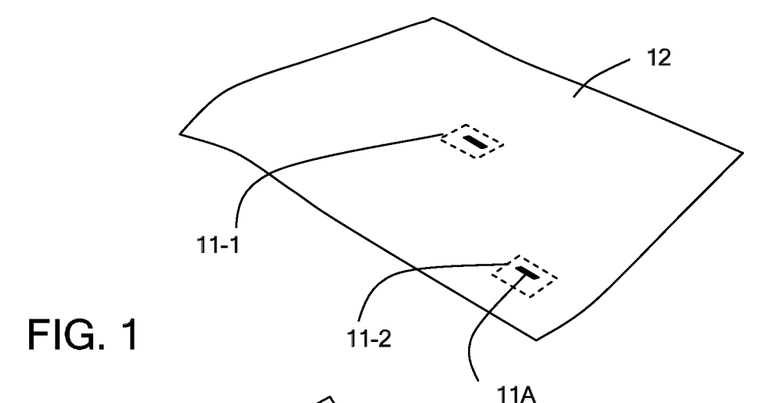
FIG. 1 is an isometric top view of a sensor pad illustrating sensor modules with RFID tag sensors top.

FIG. 1 refers to two RFID sensor modules 11 located strategically on a flexible, cleanable sensor pad 12 made of medical grade polymer such as silicone rubber or equivalent sanitation approved material compatible to this system.

Figure 2:
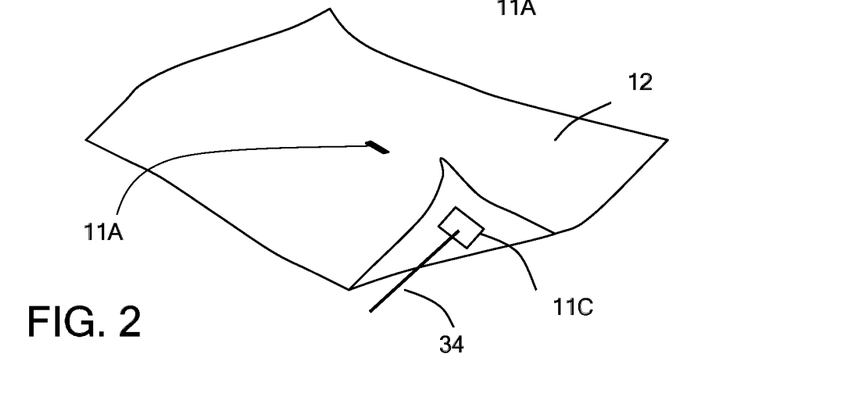
FIG. 2 is a bottom isometric view of the sensor pad with sensor module antenna visible.

FIG. 2 shows the top and bottom of a sensor module in relation to the sensor pad. Sensor tag 11A is shown on top of the sensor pad 12 as the top part of sensor module 11-1 at the center. External antenna 11C of Module 11-2 at the right lower location is shown on the bottom of the sensor pad 12. A common wire 34 connects antennas 11C of Module 11-2 and other external antennas to a transceiver.

Figure 3:
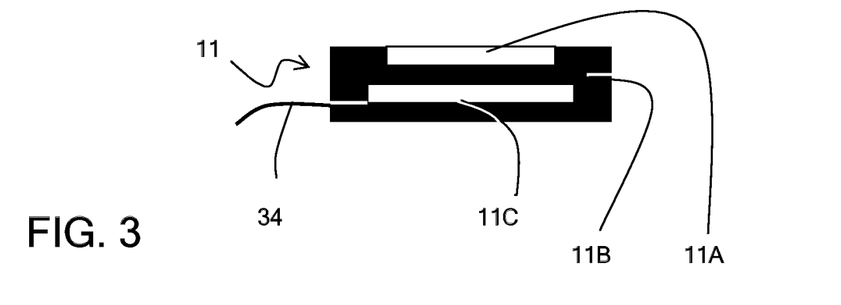
FIG. 3 is a cross-sectional elevation of each sensor module.

FIG. 3 is a cross sectional view of the sensor module 11 as embedded in the sensor pad 12 where 11A is the sensor tag; 11C is the antenna and 11B is a RF transparent insulating material. This module 11 is embedded in the sensor pad 12. Even though one sensor module 11 can detect incontinence moisture, two or more modules 11 located at a distance within the sensor pad 12 can supply redundancy and error detection to enhance the fidelity of the resultant incontinence determination. Wire 34 connects antennas 11C of each module 11 to the mating RFID controller-transceiver 26 located elsewhere under the hospital bed 134.

Figure 4:
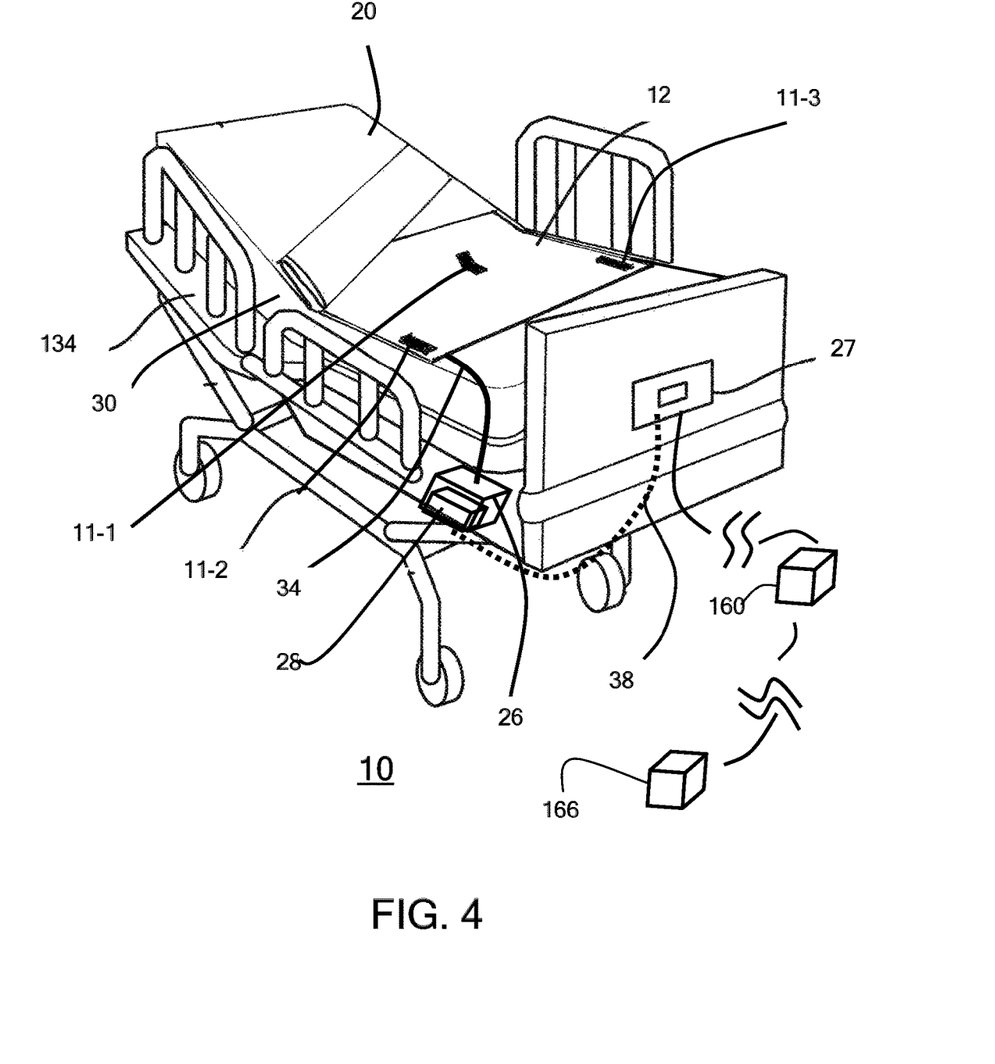
FIG. 4 is an illustration of the sensor pad deployed on a hospital bed.

FIG. 4 is an illustration of the sensor pad 12 deployed on a typical hospital bed 134. This sensor pad 12 is populated with three sensor modules 11. The sensor pad 12 is shown on top of the mattress 20 and below a bed sheet. Here the bed sheet 20 is partially rolled up to reveal sensor pad 12. RFID sensor tag embedded modules 11-1, 11-2 and 11-3 are shown on the sensor pad 12. The RFID antenna wire bundle 34 of three external antennas 11C at the bottom of each respective sensor module exit below the sensor pad 12 to be connected to a system controller-transceiver 26 located elsewhere under the hospital bed. As mentioned previously, two or more sensor modules 11 are preferred over one. A typical hospital bed 134 will be equipped with a bed control console 27 for bed attitude and communication tasks essential to patient health monitoring and well-being.

Figure 5:
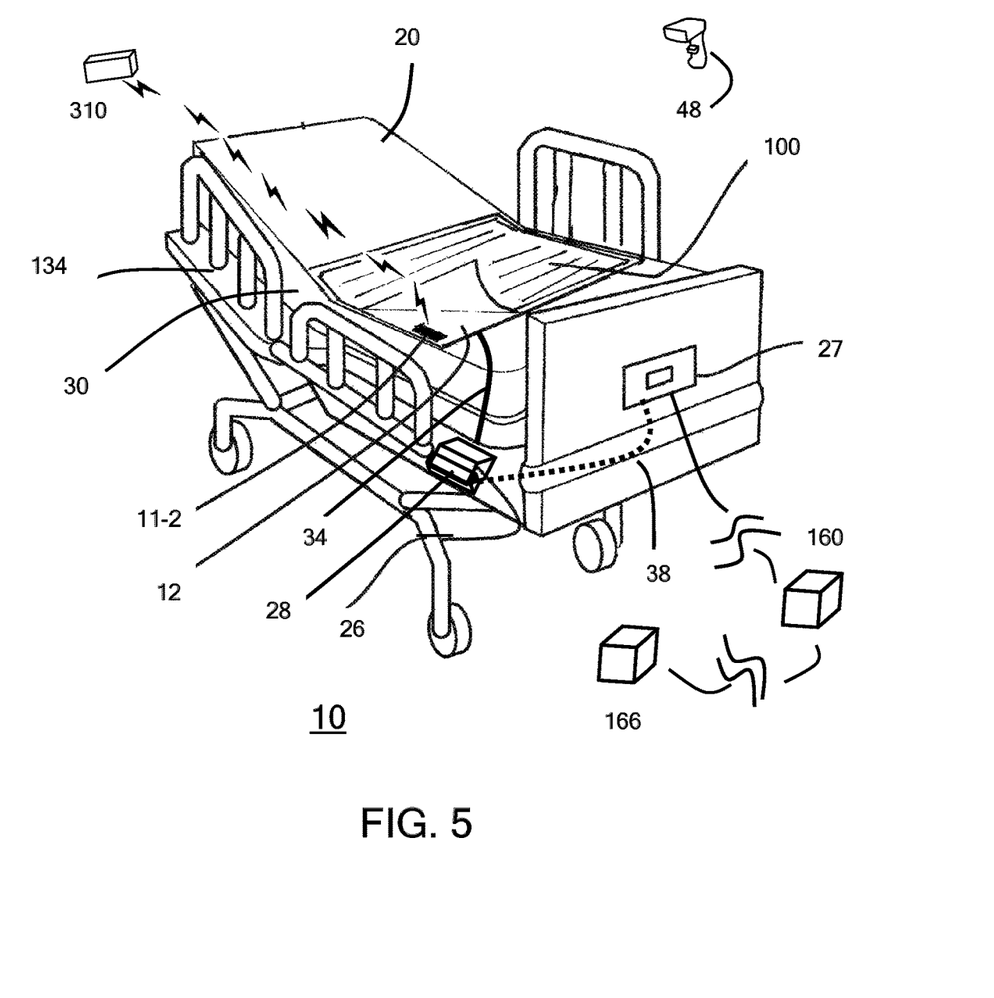
FIG. 5 is an illustration of the intelligent incontinence monitor system installation on a typical hospital bed wherein the absorbent article is an underpad.
Figure 6:
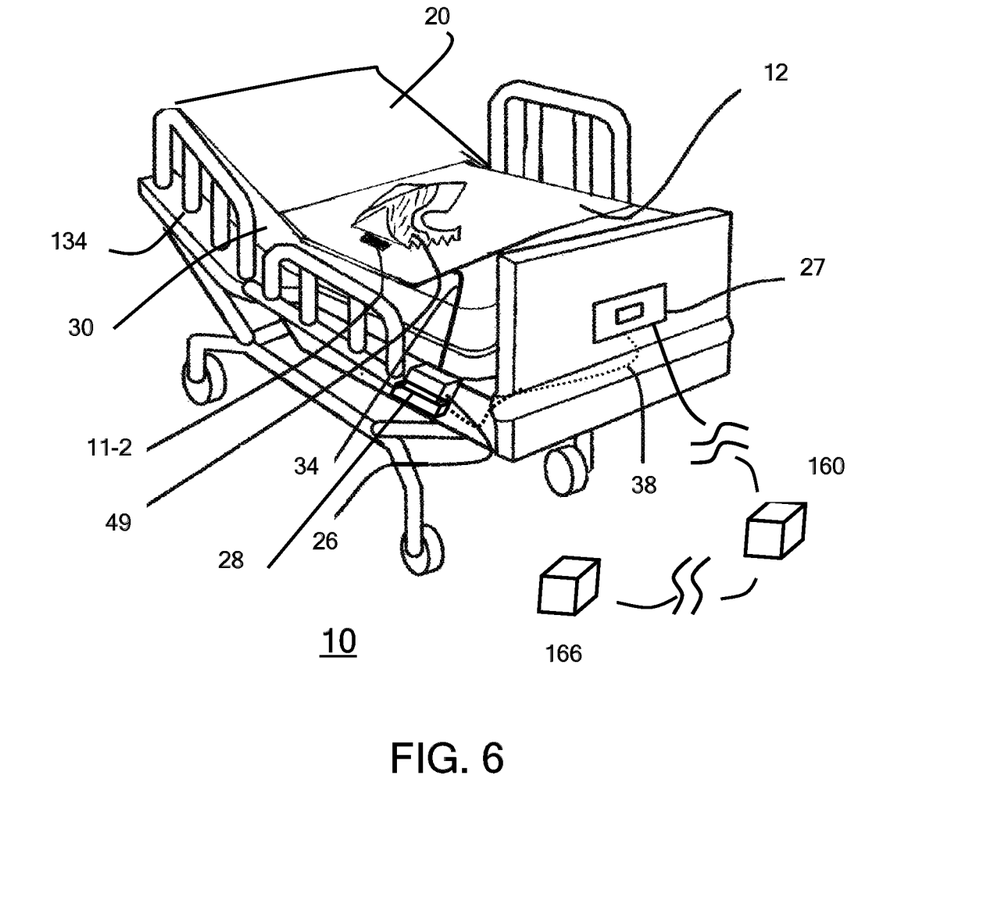
FIG. 6 is an illustration of the intelligent incontinence monitor system installation on a typical hospital bed wherein the absorbent article is a diaper.

FIG. 5 is a comprehensive system view of this intelligent incontinence monitor system 10 deployed in a typical hospital bed 134. This system is designed for hospitals using absorbent underpads 100. Absorbent underpad 100 is shown with its lower right corner turned up to reveal the aligned sensor pad 12. RFID sensor module 11-2 is noted on the sensor pad 12 at a corresponding corner along with the antenna wire bundle 34 going to the controller-transceiver 26. Other sensor modules 11 such as sensors 11-1 and 11-3 in FIG. 4 are hidden below the absorbent underpad 100. Each RFID tag sensor in sensor module 11 can be of moisture, temperature, pressure, pH, gas or other designs for sensing corresponding physical attributes to report presence and signal level of each attribute to the controller-transceiver 26. Sensor modules 11-1, 11-2, and 11-3 can be programmed for room ID when the system sensor pad 12 is installed for the first time. Depending on hospital information system requirements, patient ID, and other data needed for incontinence alarm entry into the hospital information system can be additionally programmed into the sensor modules 11 and former bed occupant data erased using a compatible handheld RFID Reader-writer 48. However, each RFID module 11 can be alternatively programmed using the system controller-transceiver 26 if the system is ordered with WIFI or Bluetooth options. A keypad in a typical cell phone 310 connected with the controller-transceiver 26 via WIFI or Bluetooth to write and read back medical record number or other ID data to each RFID sensor with the needed security code programmed into the controller-transceiver 26. Ideally, controller-transceiver 26 will be connected to the hospital information system network. Cell phone access to RFID sensor modules will be restricted to authorized staff. Hospital network 160 connection is also ideally connected to bed control console 27 or wherever else the network is located via wire 38, or wirelessly with WIFI or Bluetooth. Detection and signal level of tracked physical attribute data supplied by each RFID tag sensor module 11 will be processed and adjudicated for incontinence by the controller-transceiver 26 using custom digital signal processing algorithms. Controller on-off, reset and status of ready, error and armed is displayed on panel 28 on the controller-transceiver 26. Data transmission to the hospital information system 160 consists primarily of an alarm signal sent via wire 38 or wirelessly using WIFI or Bluetooth to the bed command console 27 to notify hospital personnel of an incontinence event having occurred with the patient monitored. This alarm signal can be addressed to a nurses' station 166 in general or to any particular nurse or aid in charge of incontinence mitigation, programmable per hospital direction. Other useful data can include timing of event, accounting and tracking recording of absorbent pad replacement or more for evaluative metrics.

FIG. 6 is an alternate embodiment view of this intelligent incontinence monitor designed for hospitals using absorbent adult diapers 49. Diaper type absorbent article 49 shown here is the lower half, which will contact a patient's body (not shown). Sensor module 11-2 is located strategically on sensor pad 12 closer to the diaper 49 as opposed to the example in FIG. 5 where this sensor pad 12 is designed for the more likely situation for hospitals allowing only absorbent underpads 100. As before, sensor module antenna 11C is wired to the controller-transceiver 26 located under the bed. The controller-transceiver 26 is itself connected via wire 38 or wirelessly using WIFI or Bluetooth to the bed command console 27, similar to the embodiment in FIG. 5. Data transmission to the hospital information system 160 consists primarily of an alarm signal to notify hospital personnel of an incontinence event having occurred with the patient monitored. This alarm signal can be addressed to the nurses' station 166 in general or to any particular nurse or aide in charge of incontinence mitigation, programmable per hospital direction. Other useful data can include timing of event, accounting, and tracking recording of absorbent pad replacement or more for evaluative metrics.

Figure 7:
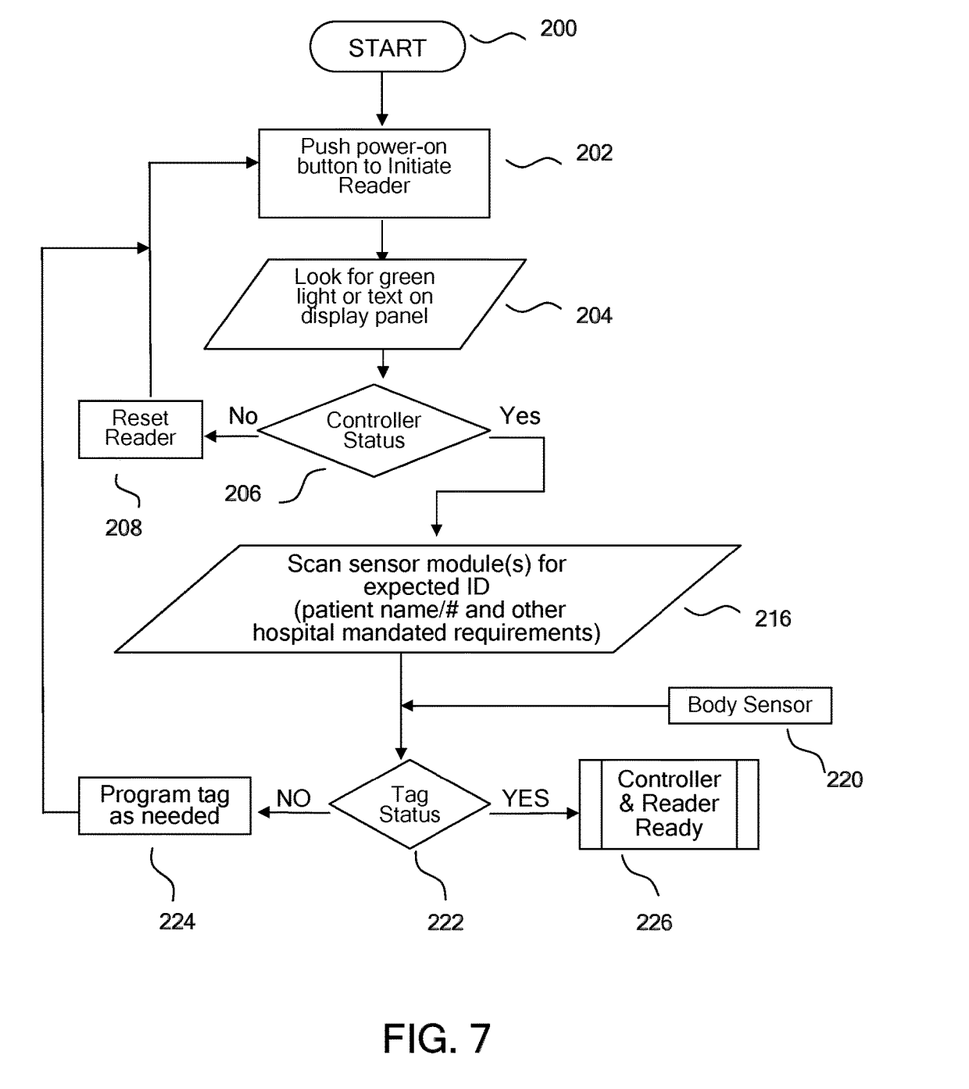
FIG. 7 is a flow diagram of the dynamic initiation operation of the present system.

FIG. 7 is a controller process flow diagram to describe how the intelligent incontinence monitor system 10 can recognize incontinence and screen out false positive incontinence signals before activating the alarm. Physical performance is summarized first. The controller 26 is in charge of acquiring inputs and forwarding feedback to the sensor modules 11. In an initiation, or new patient mode or a reset mode in which the absorbent article is replaced, the nurse-caregiver presses a button on the controller status panel 28 or uses a cell phone 310 app if WIFI or Bluetooth is ordered for the system. With a center sensor module 11-1 on the sensor pad 12, incontinence scanning will not start until the sensor, which doubles as a body sensor, reports a human body profile to the controller 26. This body sensor also pauses scanning in situations where the patient is out of the bed for whatever reason, but will resume as soon as it senses a body again. A green light or an appropriate text display at the controller-transceiver panel 28 or an indication on the cell phone will be set to indicate start of normal incontinence scanning. This system 'on' signal can also optionally send a message to the hospital network 160 that the incontinence system is in normal operating mode. Short of a deactivated system, the nurse-caregiver will receive audio/visual feedback if system initiation fails in the form of a red light, blinking, or beeping etc., to include displayed text on the controller panel 28 as chosen by the hospital as part of customized installation of the intelligent incontinence monitor system 10. The first step for re-initiation is to reset the controller 26 after all the connections are verified to be in place. Other diagnostic failures include detection that sensor tags do not have patient or the most basic hospital room data, or that other required turn-on requirements mandated by hospital rules are not met. One example of an additional hospital mandate is that a body must be on the bed before system stays on to limit radio frequency (RF) emission in the hospital room. An RF signal quiet interval is provided between RF-on intervals. Intermittent RF operation with a 20% duty cycle will cut down RF emission by 4/5, or 80%.

In FIG. 7, operation begins at block 200. At block 202, a power-on button initiates operation of the controller 26 (FIG. 4). At block 204, an operator checks for the display, e.g., a green light, indicative of activation of the controller 28. At block 206, activation of the controller 26 is sensed. If the controller 26 is not activated, then at block 208, the controller is reset, and operation returns to block 202. If the controller is activated, operation proceeds to block 216. The sensor modules 11 are scanned to determine if hospital-mandated information has been encoded. Additionally, a body sensor output produced at block 220 is sensed. The status of each tag is evaluated at block 222. If further sensor programming is needed, further programming is commanded at block 224, and operation returns to block 202. If the required patient information is present, the controller 26 is ready, and at block 226, further scanning is enabled.

Figure 8:
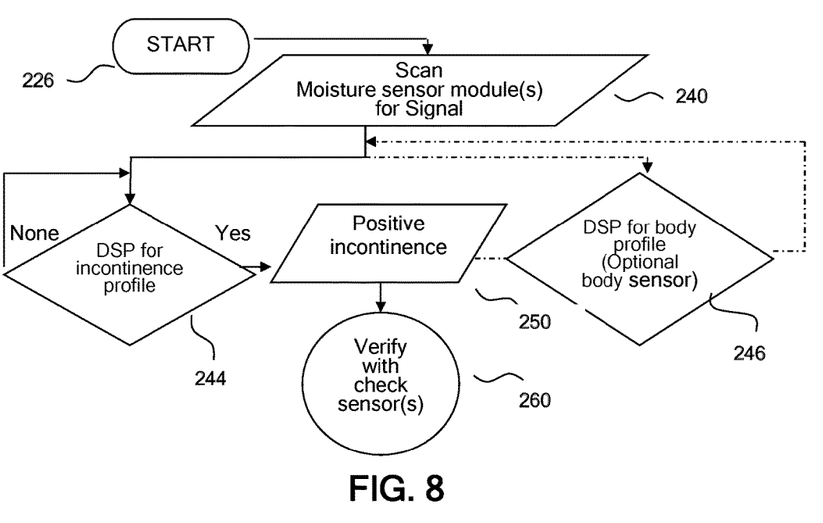
FIG. 8 is a flow diagram of management of incontinence moisture scanning.

FIG. 8 comprises a logical flow diagram of controller-transceiver 26 (FIG. 5) scanning for sensor inputs. FIG. 8 illustrates management of incontinence moisture scanning. At block 240, the RFID moisture sensor module 11-2 (FIG. 5 and FIG. 6) sends signals to the controller-transceiver 26. At block 244, a diffusion digital signal processing (DSP) algorithm with time and saturation level variables is executed. The output indicative of the algorithm result is compared to a stored incontinence moisture profile. This step operates to guard against false positives. A false positive could result, for example, from the presence of a body appendage in the range of the moisture sensor 11. A multiple sensor pad 12 configuration with a central body sensor 11-1 (FIG. 4), which is optional, will improve upon spurious positives by determining the positioning of the patient and diffusion rate from one module to the next.

A positive sensor profile is generated for every brand and model of absorbent pad used by the subscriber hospital. A moisture profile is a plot of time and diffusion rate obtained with a known volume of urine discharge passing through the sensor which would result in a typical "wet" absorbent pad designation that merits changing. Similarly, a temperature profile is a plot of time and cooling rate obtained with a known volume of urine discharge passing through the sensor which would result in a "wet" absorbent pad determination. A DSP algorithm defines each profile. Sample trigger profiles are obtained in a laboratory or a clinical trial situation. Only minimal recalibration is required where alarm trigger level is adjusted in situ in a new subscriber hospital to match its chosen brand of absorbent articles; and, if necessary, to its acceptable "wet" level definition.

Figure 9:
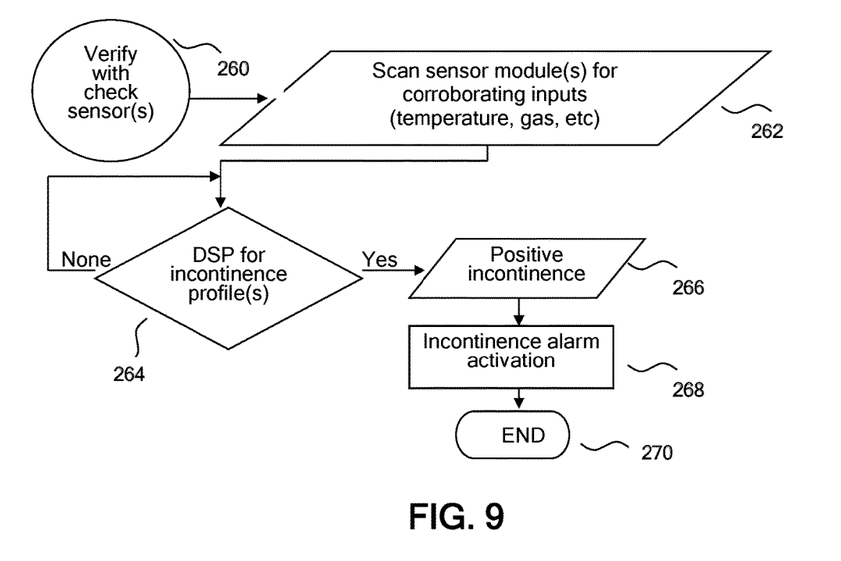
FIG. 9 is a flow diagram of management of redundant incontinence sensors scanning for inputs other than moisture.

FIG. 9 comprises the scanning of redundant sensors for confirmation of a positive indication of an incontinence event. Scan data from checks sensors are evaluated at block 262. Comparison to incontinence profiles is performed at block 264. If no event is detected, operation returns to the input of block 262 for continuous querying. If a positive determination of incontinence is found at block 266, an output is provided to activate an incontinence alarm at block 268. At block 270, operation is complete.

The present implementation of redundant sensor cross verification whereby sensor modules based on different physical attributes serve to cross check the initial moisture data minimizes false positive triggering. Other than moisture, physical attributes that can characterize incontinence discharge include temperature, color, salinity, pH, gas and others while RFID tag sensors are available to pick up these physical attribute characteristics. Depending on which types of auxiliary sensors are active, DSP algorithms are loaded into the controller to verify the initial determination by the moisture sensor that there is incontinence. An example of a redundant DSP algorithm is temperature, whereby time and temperature value variables can describe an incontinence event temperature profile. Given that an incontinence discharge from a body must be warmer than ambient hospital room temperature, an RFID tag temperature sensor will detect the temperate rise and fall of moisture passing through the sensor. Thus, a logical "if-then" cross check with a different physical attribute would minimize false alarms.

Only when data profile matches are adjudicated by a logic and experience-based arbitration algorithm will the controller provide the incontinence alarm. An alarm signal per predetermined instructions stored in the sensor patient ID data bank and controller memory will be forwarded in the required protocol to the hospital information network. The hospital information system network 160 will send the incontinence alarm to specific attendant nurse or staff, while the hospital Patient Records Department may want to have the alarm occurrence and frequency logged into the patient's hospital record for medical and/or service audit use. A hospital accounting department may also want a record of each absorbent article used for billing purposes. There could be more notifications required and each may require its own protocol. The controller processor can be scaled, selected, and upgraded as necessary to handle even more complexity. This system is both versatile and flexible.

The invention claimed is:

1. An incontinence monitoring system comprising:
a plurality of sensor modules, each said sensor module being powered by resonant frequency signals;
each said sensor module further comprising an RFID sensor tag and producing condition- responsive data; each said sensor module also further comprising a first wired transceiver antenna and a second wireless RFID sensor tag embedded antenna;
each said sensor module being dormant in the absence of RF power received from said first wired transceiver antenna in said module and said RFID sensor tag being enabled to produce the condition-responsive data by RF power received from said first wired transceiver antenna;
a waterproof substrate pad, said substrate pad having said sensor modules unitary with and embedded therein to be placed in registration with an incontinence absorbance article, said incontinence absorbance article being discrete from said substrate pad with sensor modules embedded therein;
each said sensor module comprising a detector for sensing a specific physical-environmental attribute;
each said sensor module comprising said first wired transceiver antenna and said wireless RFID sensor tag maintained in a fixed relative position and separated by an insulator;
each said sensor module being selected to sense at least one specific physical-environmental detection attribute and positioned in the substrate pad at a preselected location;
each said sensor module being powered-on separately by a respective wired transceiver antenna, whereby data transmission interference is avoided, said each powered sensor module being scanned individually in sequence for parametric changes indicative of stimulation by its preselected physical-environmental attribute;
a controller memory storing at least one preselected profile, each said preselected profile relating the at least one specific physical-environmental attribute to data indicative of an incontinence event, said controller memory having locations storing preselected algorithms for executing comparisons of said sensor data to the at least one preselected profile;

said algorithms utilizing redundant and differing physical-environmental parameters each indicative of an incontinence event; and a voting circuit to determine when to trigger an alarm.

2. The system according to claim 1 wherein said substrate pad is integral with a hospital bed, whereby said substrate pad will be located below a bed sheet.

3. The system according to claim 1 wherein each said RFID sensor tag further comprises a programmable memory and processor integrated circuit RFIC.

4. The system according to claim 1 further comprising a system-controller transceiver wherein each first wired transceiver antenna in the sensor modules is directly wired to said system controller-transceiver.

5. The system according to claim 3 wherein each said RFID sensor tag comprising the second wireless RFID sensor tag embedded antenna coupled wirelessly to a matching corresponding first wired transceiver antenna to receive RF power.

6. The system according to claim 3 wherein said RFID sensor tag further comprises a capacitor element to store received power.

7. The system according to claim 3 wherein each second wireless RFID sensor tag embedded antenna is formed to report impedance in response to a selected physical-environmental parameter.

8. The system according to claim 4 wherein said system controller-transceiver is configured to provide a selectable duty cycle and pulse width adjustment of RF power.

9. The system according to claim 8 wherein said system controller-transceiver is configured to provide a lowest operating power and pulse width in response to a determination of patient absence.

10. The system according to claim 1 further comprising an alarm signal generator forming an alarm signal comprising an alarm trigger and providing preselected data available for audit.

11. The system according to claim 1 wherein the substrate pad is positionable below a bed sheet and in registration with the incontinence absorbance article to be located on top of a bedsheet and an expected position of a discharge orifice of the patient.

12. An incontinence monitoring system comprising:
a plurality of sensor modules, each said sensor module comprising an RFID tag sensor being powered by a wired external antenna;
each said sensor module comprising the RFID tag sensor for sensing a specific parameter and producing condition-responsive data;
a waterproof substrate pad, said substrate pad having said sensor modules mounted therein to be placed in registration with an incontinence absorbance article;
said wired external antenna and said RFID sensor in each said sensor module being maintained in a fixed relative position inside said substrate pad, said substrate pad comprising an insulator separating said wired external antenna and said RFID tag sensor;
a controller memory storing profiles, each said profile correlating a parameter to data indicative of an incontinence event, said controller memory having locations storing preselected algorithms for executing comparisons of parameter values to a profile; said algorithms utilizing selected parameters, each parameter having a correlation with an incontinence event.

13. The system according to claim 12 wherein the substrate pad is populated with multiple sensor modules, said sensor modules being relatively positioned to provide information in addition to moisture level.

14. The system according to claim 12 wherein the plurality of said sensor modules provides redundant determinations of an incontinence alarm condition.

15. The system according to claim 12 wherein digital signal processing (DSP) of moisture absorbance and diffusion algorithms evaluate moisture volume determination.

16. The system according to claim 12 wherein one said sensor module senses body moisture to report bed occupancy status.

17. The system according to claim 14 wherein algorithms are adjusted to measure selected attributes of a particular absorbent article.

18. The system according to claim 13 wherein one said sensor module is located to be in registration with a patient and located to be responsive to impedance change at a patient location, whereby a bed occupancy status may be reported.

19. The system according to claim 12 wherein parametric data acquired by each sensor module are sent to the controller memory.

20. The system according to claim 17 wherein an output generated by a diffusion signal processing algorithm in each said sensor module is compared to a stored incontinence moisture profile.

21. The system according to claim 16 wherein triggered condition-response outputs from different sensor modules are compared to a stored physical-environmental data set corresponding to a profile of condition-responsive data.

22. The system according to claim 19 wherein an alarm response is triggered by a controller in response to a voting determination that an incontinence event has occurred.

23. The system according to claim 22 wherein the incontinence event alarm response is selectively sent by wire or wirelessly.

24. The system according to claim 22 wherein the incontinence event alarm response is sent to designated staff for incontinence remediation and/or automated journal entries.

25. The system according to claim 22 wherein the alarm response is configured to be integrated into hospital records, and wherein the alarm response continues until reset, the reset being accomplished by removal of the alarm condition.

* * * * *